US012635906B2

(12) United States Patent
Matsumoto et al.

(10) Patent No.: US 12,635,906 B2
(45) Date of Patent: May 26, 2026

(54) ACTION STATE ESTIMATION APPARATUS, ACTION STATE ESTIMATION METHOD, ACTION STATE LEARNING APPARATUS, AND ACTION STATE LEARNING METHOD

(71) Applicant: Murata Manufacturing Co., Ltd., Nagaokakyo (JP)

(72) Inventors: Tatsuhiko Matsumoto, Nagaokakyo (JP); Atsushi Naito, Nagaokakyo (JP); Naoki Kawara, Nagaokakyo (JP); Yutaka Takamaru, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 703 days.

(21) Appl. No.: 18/156,545

(22) Filed: Jan. 19, 2023

(65) Prior Publication Data

US 2023/0148908 A1 May 18, 2023

Related U.S. Application Data

(63) Continuation of application No. PCT/JP2021/027254, filed on Jul. 21, 2021.

(30) Foreign Application Priority Data

Jul. 30, 2020    (JP) ................................ 2020-129387
Jul. 30, 2020    (JP) ................................ 2020-129388

(51) Int. Cl.
*A61B 5/11*      (2006.01)
*A61B 5/00*      (2006.01)

(52) U.S. Cl.
CPC .......... *A61B 5/1107* (2013.01); *A61B 5/1101* (2013.01); *A61B 5/7264* (2013.01); *A61B 5/7267* (2013.01)

(58) Field of Classification Search
CPC ... A61B 5/1107; A61B 5/1101; A61B 5/7264; A61B 5/7267
See application file for complete search history.

(56) References Cited

U.S. PATENT DOCUMENTS 7,623,944 B2    11/2009   Dariush
9,402,579 B2    8/2016   Mcleod et al.
(Continued)

FOREIGN PATENT DOCUMENTS

JP      200278697 A    3/2002
JP      2003116822 A    4/2003
(Continued)

OTHER PUBLICATIONS

International Search Report in PCT/JP2021/027254, mailed Oct. 12, 2021, 4 pages.
(Continued)

*Primary Examiner* — Reginald A Renwick
(74) *Attorney, Agent, or Firm* — ArentFox Schiff LLP

(57) ABSTRACT

An action state estimation apparatus is provided that includes a sampling portion, a statistic calculation portion, an action state model storage, and an estimation calculation portion. The sampling portion samples a displacement measurement signal within a predetermined time and generates displacement measurement data. The statistic calculation portion calculates a statistic of the displacement measurement data. The action state model storage stores an action state model modeled by associating the statistic with a loaded state of a muscle of the test subject. The estimation calculation portion estimates the loaded state by setting the statistic as an input vector and using the action state model.

21 Claims, 16 Drawing Sheets

(56) References Cited

U.S. PATENT DOCUMENTS

| | | | |
|---|---|---|---|
| 11,617,527 | B2 | 4/2023 | Majava et al. |
| 12,011,257 | B2 | 6/2024 | Matijevich et al. |
| 2017/0043215 | A1 | 2/2017 | Peterson et al. |
| 2021/0366602 | A1 | 11/2021 | Huang et al. |

FOREIGN PATENT DOCUMENTS

| | | | |
|---|---|---|---|
| JP | 2006345990 | A | 12/2006 |
| JP | 2007160076 | A | 6/2007 |
| JP | 2011182824 | A | 9/2011 |
| JP | 201697228 | A | 5/2016 |
| JP | 2017-023449 | A | 2/2017 |
| JP | 201842998 | A | 3/2018 |
| WO | 2019/130840 | A1 | 7/2019 |

OTHER PUBLICATIONS

International Search Report in PCT/JP2021/027255, mailed Oct. 12, 2021, 4 pages.
Takanokura et al., "Mechanism of physiological tremor in upper limb and its application for evaluation of fatigue," The University of Electro-Communications, 2001, vol. 37, Retrieved from the Internet: <URL: https://www.jstage.jst.go.ip/article/jje1965/37/Supplement/37_Supplement_274/_article/-char/ja/>, pp. 274-275, (cited in International Search Report).

| LEVEL OF IMPORTANCE | MUCLE M1 | MUCLE M2 | MUCLE M3 | MUCLE M4 |
|---|---|---|---|---|
| 1ST | A1 | A3 | A5 | A4 |
| 2ND | A2 | A5 | A13 | A11 |
| 3RD | A8 | A2 | A3 | A1 |
| 4TH | A12 | A14 | A2 | A3 |
| 5TH | A7 | A15 | A9 | A6 |

| TIME | t1 | t2 | t3 | t4 | · · · · · | t98 | t99 | t100 |
|---|---|---|---|---|---|---|---|---|
| SIGNAL STRENGTH | 1.5 | 1.9 | 4.2 | 0.3 | · · · · · | 3.6 | 2.0 | 1.3 |

FIG.6B

| RANK | R1 | R2 | R3 | R4 | · · · · · | R98 | R99 | R100 |
|---|---|---|---|---|---|---|---|---|
| SIGNAL STRENGTH | 4.2 | 4.0 | 4.0 | 3.6 | · · · · · | 0.4 | 0.4 | 0.3 |

FIG.6C

| STRENGTH BLOCK | B1 | B2 | B3 | · · · · · | B9 | B10 |
|---|---|---|---|---|---|---|
| INTEGRATED VALUE | 40.2 | 33.5 | 21.8 | · · · · · | 15.2 | 6.7 |

| LEVEL OF IMPORTANCE | MUSCLE M1 | MUSCLE M2 | MUSCLE M3 | MUSCLE M4 |
|---|---|---|---|---|
| 1ST | B10 | B10 | B3 | B7 |
| 2ND | B9 | B8 | B8 | B6 |
| 3RD | B6 | B9 | B1 | B10 |
| 4TH | B3 | B7 | B2 | B8 |
| 5TH | B5 | B1 | B10 | B9 |

| TIME | t1 | t2 | t3 | · · · | t10 | · · · | t91 | · · · | t99 | t100 |
|---|---|---|---|---|---|---|---|---|---|---|
| SIGNAL STRENGTH | 1.5 | 1.9 | 4.2 | · · · | 0.3 | · · · | 2.6 | · · · | 2.0 | 1.3 |

FIG.8B

| TIME BLOCK | B1t | B2t | B3t | · · · · · | B9t | B10t |
|---|---|---|---|---|---|---|
| AVERAGE VALUE | 3.01 | 2.23 | 1.42 | · · · · · | 1.28 | 2.13 |

FIG.8C

| TIME BLOCK | B1t | B2t | B3t | · · · · · | B9t | B10t |
|---|---|---|---|---|---|---|
| INTEGRATED VALUE | 30.1 | 22.3 | 14.2 | · · · · · | 12.8 | 21.3 |

FIG.10A

| LEVEL OF IMPORTANCE | MUSCLE M1 | MUSCLE M2 | MUSCLE M3 | MUSCLE M4 |
|---|---|---|---|---|
| 1ST | Ar1 | Ar3 | Ar5 | Ar4 |
| 2ND | Ar2 | Ar5 | Ar13 | Ar11 |
| 3RD | Ar8 | Ar2 | Ar3 | Ar1 |
| 4TH | Ar12 | Ar14 | Ar2 | Ar3 |
| 5TH | Ar7 | Ar15 | Ar9 | Ar6 |

FIG.10B

| LEVEL OF IMPORTANCE | MUSCLE M1 | MUSCLE M2 | MUSCLE M3 | MUSCLE M4 |
|---|---|---|---|---|
| 1ST | Aa1 | Aa3 | Aa5 | Aa4 |
| 2ND | Aa2 | Aa5 | Aa13 | Aa11 |
| 3RD | Aa8 | Aa2 | Aa3 | Aa1 |
| 4TH | Aa12 | Aa14 | Aa2 | Aa3 |
| 5TH | Aa7 | Aa15 | Aa9 | Aa6 |

FIG.14A

| LEVEL OF IMPORTANCE | MUSCLE M1 | MUSCLE M2 | MUSCLE M3 | MUSCLE M4 |
|---|---|---|---|---|
| 1ST | Br10 | Br10 | Br3 | Br7 |
| 2ND | Br9 | Br8 | Br8 | Br6 |
| 3RD | Br6 | Br9 | Br1 | Br10 |
| 4TH | Br3 | Br7 | Br2 | Br8 |
| 5TH | Br5 | Br1 | Br10 | Br9 |

FIG.14B

| LEVEL OF IMPORTANCE | MUSCLE M1 | MUSCLE M2 | MUSCLE M3 | MUSCLE M4 |
|---|---|---|---|---|
| 1ST | Ba10 | Ba10 | Ba3 | Ba7 |
| 2ND | Ba9 | Ba8 | Ba8 | Ba6 |
| 3RD | Ba6 | Ba9 | Ba1 | Ba10 |
| 4TH | Ba3 | Ba7 | Ba2 | Ba8 |
| 5TH | Ba5 | Ba1 | Ba10 | Ba9 |

ACTION STATE ESTIMATION APPARATUS, ACTION STATE ESTIMATION METHOD, ACTION STATE LEARNING APPARATUS, AND ACTION STATE LEARNING METHOD

CROSS REFERENCE TO RELATED APPLICATIONS

This application is a continuation of PCT Application No. PCT/JP2021/027254, filed Jul. 21, 2021, which claims priority to Japanese Patent Application No. 2020-129387, filed Jul. 30, 2020, and Japanese Patent Application No. 2020-129388, filed Jul. 30, 2020, the entire contents of each of which are hereby incorporated by reference in their entirety.

TECHNICAL FIELD

The present invention relates to a system and method for estimating an action state including a loaded state of a muscle from a detection result of a tremor and a system and method (e.g., an action state learning technology) of generating an action state model for such an estimation technology.

BACKGROUND

Japanese Patent Application Publication No. 2011-182824 (hereinafter "Patent Literature 1") discloses an action state estimation apparatus that converts a measurement signal of a displacement detection sensor into a frequency component. The action state estimation apparatus disclosed in Patent Literature 1 estimates an action state from a component of a predetermined frequency band.

However, conventional apparatus and method that are shown in Patent Literature 1 need to convert a measurement signal of a sensor into a frequency component. Therefore, a processing load to generate the estimation signal increases.

SUMMARY OF THE INVENTION

Therefore, it is an object of the present invention to provide an action state estimation system and method that significantly reduces a processing load while achieving a desired estimation accuracy.

In an exemplary aspect, an action state estimation apparatus is provided that includes a first sampling portion, a first statistic calculation portion, an action state model storage, and an estimation calculation portion. The first sampling portion samples a displacement measurement signal of a test subject within a predetermined time and generates displacement measurement data. Moreover, the first statistic calculation portion calculates a first statistic of the displacement measurement data. The action state model storage stores an action state model modeled by associating the first statistic with a loaded state of a desired muscle. The estimation calculation portion estimates the loaded state by setting the first statistic as an input vector and using the action state model.

In this configuration, the loaded state is estimated by directly using the displacement measurement data. As a result, the processing load is significantly reduced while the desired estimation accuracy is achieved.

BRIEF DESCRIPTION OF DRAWINGS

FIG. 2 is a table showing an example of a setting of a level of importance according to the first exemplary embodiment.

FIG. 6A shows an example of time variation of signal strength, FIG. 6B shows signal strength distribution, and FIG. 6C shows strength block data.

FIG. 7 is a table showing an example of a setting of a level of importance according to a second exemplary embodiment.

FIG. 8A shows an example of time variation of signal strength, FIG. 8B shows strength block data (an average value), and FIG. 8C is a view showing strength block data (an integrated value).

FIG. 10A and FIG. 10B are tables showing an example of a setting of a level of importance according to the third exemplary embodiment.

FIG. 14A and FIG. 14B are tables showing an example of a setting of a level of importance according to a fourth exemplary embodiment.

DETAILED DESCRIPTION OF THE EXEMPLARY EMBODIMENTS

First Exemplary Embodiment

An action state estimation technology and an action state model generation technology according to a first exemplary embodiment will be described with reference to the drawings.

(Configuration and Processing of Action State Estimation Apparatus)

Figure 1:
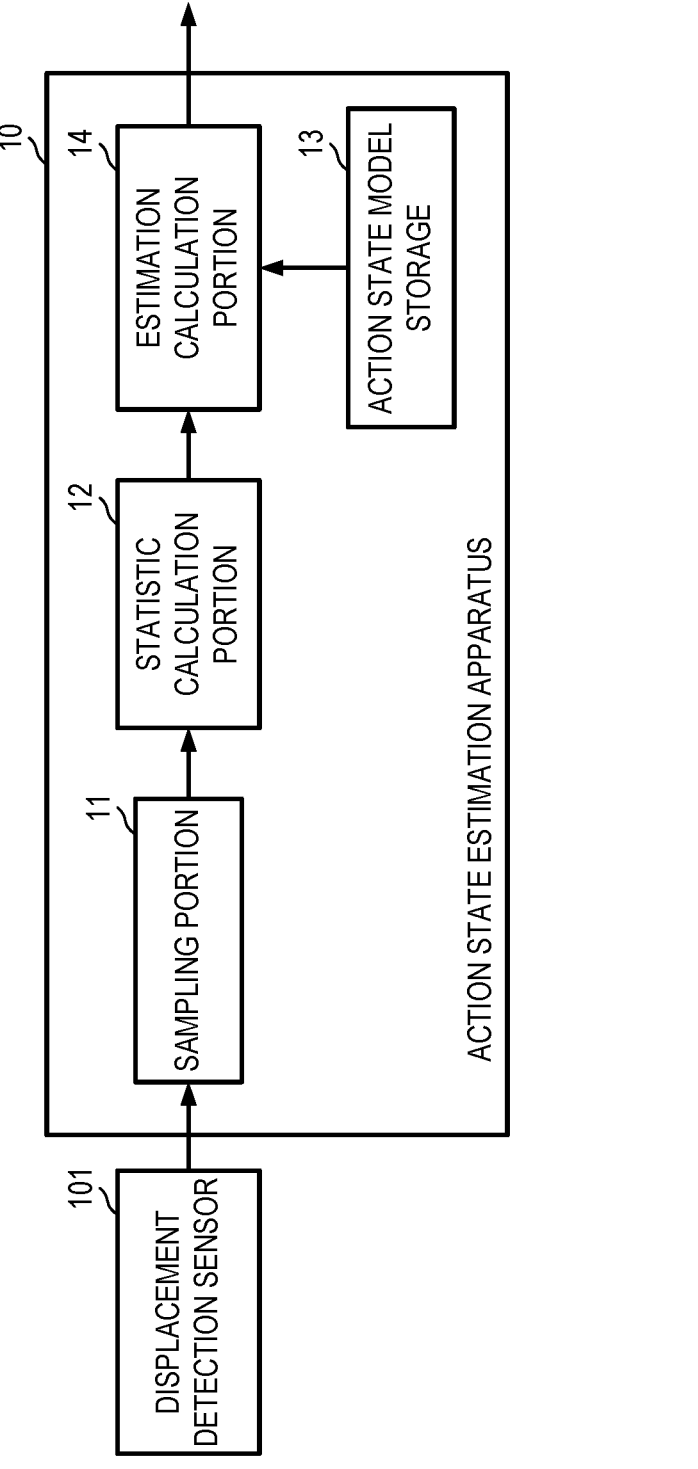
FIG. 1 is a functional block diagram of an action state estimation apparatus according to a first exemplary embodiment.

FIG. 1 is a functional block diagram of an action state estimation apparatus according to the first exemplary embodiment. As shown in FIG. 1, the action state estimation apparatus 10 includes a sampling portion 11, a statistic calculation portion 12, an estimation calculation portion 14, and an action state model storage 13. Each functional portion configuring the action state estimation apparatus 10 can be implemented as an electronic circuit, an IC, a storage medium storing a program that, when executed by a calculation processing device, is configured to perform a function of each function portion, where the calculation processing device (e.g., a CPU) is configured to execute the program.

In operation, the sampling portion 11 receives an input of a displacement measurement signal from a displacement detection sensor 101. The sampling portion 11 generates displacement measurement data by sampling the displacement measurement signal by a predetermined sampling frequency (100 Hz, for example). In other words, the sampling portion 11 generates the displacement measurement data without converting the displacement measurement signal into a frequency component. Moreover, the sampling portion 11 outputs the displacement measurement data to the statistic calculation portion 12.

It is noted that the displacement detection sensor 101 can be implemented as a piezoelectric sensor, an acceleration sensor, or the like. The displacement detection sensor 101 does not need to be disposed at a position of a muscle of which the loaded state is estimated, and may be disposed at a position at which a tremor to be produced by the muscle to be estimated is able to be measured. In addition, the displacement detection sensor 101 may be one sensor disposed at one location or can be two or more sensors disposed at two or more locations. The displacement detection sensor 101 generates and outputs a displacement measurement signal. The displacement measurement signal is a signal obtained by converting displacement on a skin surface due to tremor and deformation into the voltage.

For purposes of this disclosure, the tremor can be considered an involuntary movement that shows rhythmical muscle activity, for example. In other words, the tremor is fine and fast postural tremor seen in normal people, is called a physiological tremor, and is a frequency from 8 Hz to 12 Hz, for example. It is noted that shaking seen in an ill individual, such as a Parkinson's patient, is a pathologic tremor, is a frequency from 4 Hz to 7 Hz, for example, and is not considered as an object of the tremor in the present invention. The use of a tremor provides the following various types of advantages over myoelectric potential. For example, detection (measurement) of a tremor can be performed without a direct attachment to a surface (e.g., a skin or the like) of a body, such as a human body, to be detected. The detection of a tremor can also detect muscle contraction and expansion. The detection of a tremor can further detect a variation associated with muscle fatigue.

The statistic calculation portion 12 calculates a statistic from the displacement measurement data. In particular, the statistic calculation portion 12 calculates statistics from a plurality of displacement measurement data within a predetermined period (for 1 second, for example).

Types of statistics include, for example, an average value, a maximum value, a minimum value, a median value, a 1% value, a 5% value, a 25% value, a 75% value, a 95% value, a 99% value, a variance value, a skewness value, a kurtosis value, and an integrated value. It is noted that the types of statistics are not limited to these examples, and may be others as long as a value is obtained from time-series displacement measurement data. The statistic calculation portion 12 calculates a plurality of types of statistics out of these values. It is also noted that an x % value refers to a value located at x % counted in ascending order from the minimum value, among the plurality of displacement measurement data within a period.

The statistic calculation portion 12 then outputs the plurality of types of statistics that have been calculated, to the estimation calculation portion 14.

The action state model storage 13 stores an action state model. The action state model includes a relationship between various types of statistics of displacement measurement data and a loaded state of a muscle to be estimated. In an exemplary aspect, the action state model can previously generated by an action state learning apparatus 20 to be described below, for example, and is stored in the action state model storage 13.

The estimation calculation portion 14 estimates the loaded state of a muscle to be estimated by using the action state model stored in the action state model storage 13 and setting a plurality of statistics as an input vector. In such a case, the estimation calculation portion 14 sets a level of importance of the statistics used for estimation, according to the muscle to be estimated. This level of importance is set to the action state model, for example.

FIG. 2 is a table showing an example of a setting of a level of importance according to the first exemplary embodiment. A muscle M1, a muscle M2, a muscle M3, and a muscle M4 show a type of muscle of which the loaded state is able to be estimated by measured displacement. For example, in a case in which the displacement detection sensor 101 is disposed at a place at which tendons of an ankle are gathered, more specifically, in front of the ankle and in back of the ankle, the muscle M1, the muscle M2, the muscle M3, and the muscle M4 are able to set a soleus muscle, a gastrocnemius muscle, a tibialis anterior muscle, a quadriceps femoris muscle, a hamstring muscle, or the like. In addition, each of the statistics A1 to A15 is set to any of the above various types of statistics (e.g., the average value, the maximum value, the minimum value, the median value, the 1% value, the 5% value, the 25% value, the 75% value, the 95% value, the 99% value, the variance value, the skewness value, the kurtosis value, the integrated value, or the like).

For example, in the case of FIG. 2, with respect to the muscle M1, the level of importance to the estimation is set to an order of the statistic A1, the statistic A2, the statistic A8, the statistic A12, and the statistic A7 in order of the first place, the second place, the third place, the fourth place, and the fifth place. In addition, with respect to the muscle M2, the level of importance to the estimation is set to the order of the statistic A3, the statistic A5, the statistic A2, the statistic A14, and the statistic A15 in order of the first place, the second place, the third place, the fourth place, and the fifth place. Hereinafter, with respect to the muscle M3 and the muscle M4 as well, as shown in FIG. 2, the level of importance is set to the statistic.

The estimation calculation portion 14, when setting the muscle to be estimated, is configured to estimate a loaded state (e.g., a muscle potential value) of the muscle from the plurality of statistics, by using the level of importance that is set according to the muscle. It is noted that the loaded state of the muscle is not limited to the muscle potential value and may be any other data that is expressed as a value.

More specifically, for example, the estimation calculation portion 14 calculates an estimation result of the loaded state for each statistic that is estimated from each of the statistics ranked from the first place to the fifth place in the level of importance and the action state model. Then, the estimation calculation portion 14 weights each estimation result according to the level of importance, and calculates an estimation result of a final loaded state by performing addition averaging or the like, for example. It is also noted that the number of statistics the estimation calculation portion 14 uses for estimation is not limited to this example. For example, estimation calculation may be performed from the statistics ranked from the first place to the tenth place in the level of importance.

The estimation calculation portion 14, when the number of types of the muscle to be estimated is one, estimates a loaded state by using the statistic and the level of importance according to the muscle. On the other hand, the estimation calculation portion 14, when the number of types of the muscle to be estimated is two or more, sets a statistic and a level of importance for each muscle and estimates a loaded state with respect to each muscle.

With such a configuration, the action state estimation apparatus 10 is configured to estimate the loaded state of a muscle without performing processing to convert measurement data into a frequency component. As a result, the action state estimation apparatus 10 significantly reduces a processing load while achieving a desired estimation accuracy.

Furthermore, with such a configuration, the action state estimation apparatus 10, for each muscle to be estimated, individually sets the type of statistic used for estimation, and the level of importance. As a result, the action state estimation apparatus 10 is able to estimate the loaded state of a muscle with a higher accuracy.

In addition, with such a configuration, the action state estimation apparatus 10, even when the position of the displacement detection sensor 101 is not at a position of a muscle to be estimated, is configured to estimate the loaded state of the muscle. As a result, the action state estimation apparatus 10 is also configured to estimate the loaded state with respect to a muscle that is not appeared on a body surface or a muscle (e.g., a muscle away from a position in which the displacement detection sensor 101 is disposed, as an example) for which the muscle potential is not able to be directly measured. The displacement detection sensor 101 is disposed on an ankle, so that the action state estimation apparatus 10 is able to estimate the loaded state of a quadriceps femoris muscle, a hamstring muscle (a biceps femoris muscle, a semimembranosus muscle, a semitendinosus muscle, an adductor magnus muscle), a tibialis anterior muscle, a gastrocnemius muscle, a soleus muscle, and a gluteus maximus muscle. In addition, the action state estimation apparatus 10 is configured to estimate a linked state of a plurality of muscles.

Moreover, an effect due to an error in the position in which the displacement detection sensor 101 is disposed is able to be significantly reduced. Therefore, the disposition of the displacement detection sensor 101 is facilitated, and an operation for estimation of a loaded state is facilitated.

In addition, with such a configuration, the loaded state of a plurality of muscles can be estimated, using the displacement measurement signal of the displacement detection sensor 101 in common, so that an action state estimation system including a sensor and the action state estimation apparatus can be reduced in size.

Moreover, in such a configuration, the statistic to be used and the level of importance are individually set for each muscle to be estimated. Therefore, the action state estimation apparatus 10 is configured able to estimate the loaded state of a plurality of muscles with a high accuracy by using the displacement measurement signal of the displacement detection sensor 101 in common.

In addition, with such a configuration, a loaded state can be estimated not as a class, but as a value. In this manner, a loaded state is estimated with a value, so that the action state estimation apparatus 10 is configured to present and manage a more accurate loaded state, and is configured to provide more appropriate notification or the like, to a test subject.

(Action State Estimation Method)

Figure 3:
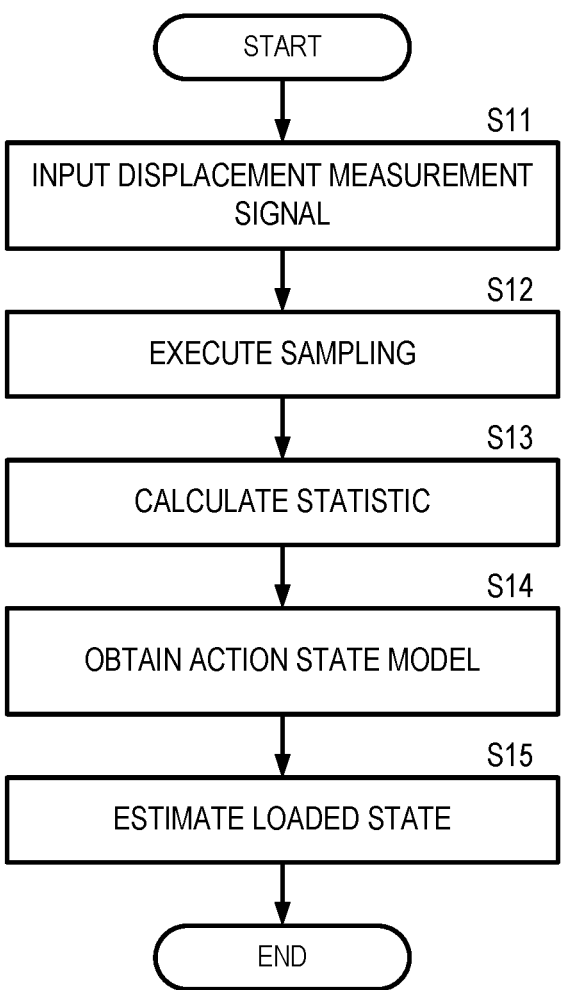
FIG. 3 is a flow chart showing a main process of an action state estimation method according to the first exemplary embodiment.

FIG. 3 is a flow chart showing a main process of an action state estimation method according to the first exemplary embodiment of the present invention. It is noted that, since the specific content of each processing is described by the above configurations, the following will be schematically described below.

The action state estimation apparatus 10 inputs a displacement measurement signal (S11). The action state estimation apparatus 10 executes sampling to the displacement measurement signal, and generates displacement measurement data (S12). The action state estimation apparatus 10 calculates a statistic from the displacement measurement data (S13).

The action state estimation apparatus 10 obtains an action state model (S14). The action state estimation apparatus 10 estimates a loaded state by using the action state model and setting the statistic as an input vector (S15).

It is also noted that the above processing may be programmed and stored in a storage medium or the like, and may be executed by an arithmetic processing apparatus such as a CPU.

(Configuration and Processing of Action State Learning Apparatus)

Figure 4:
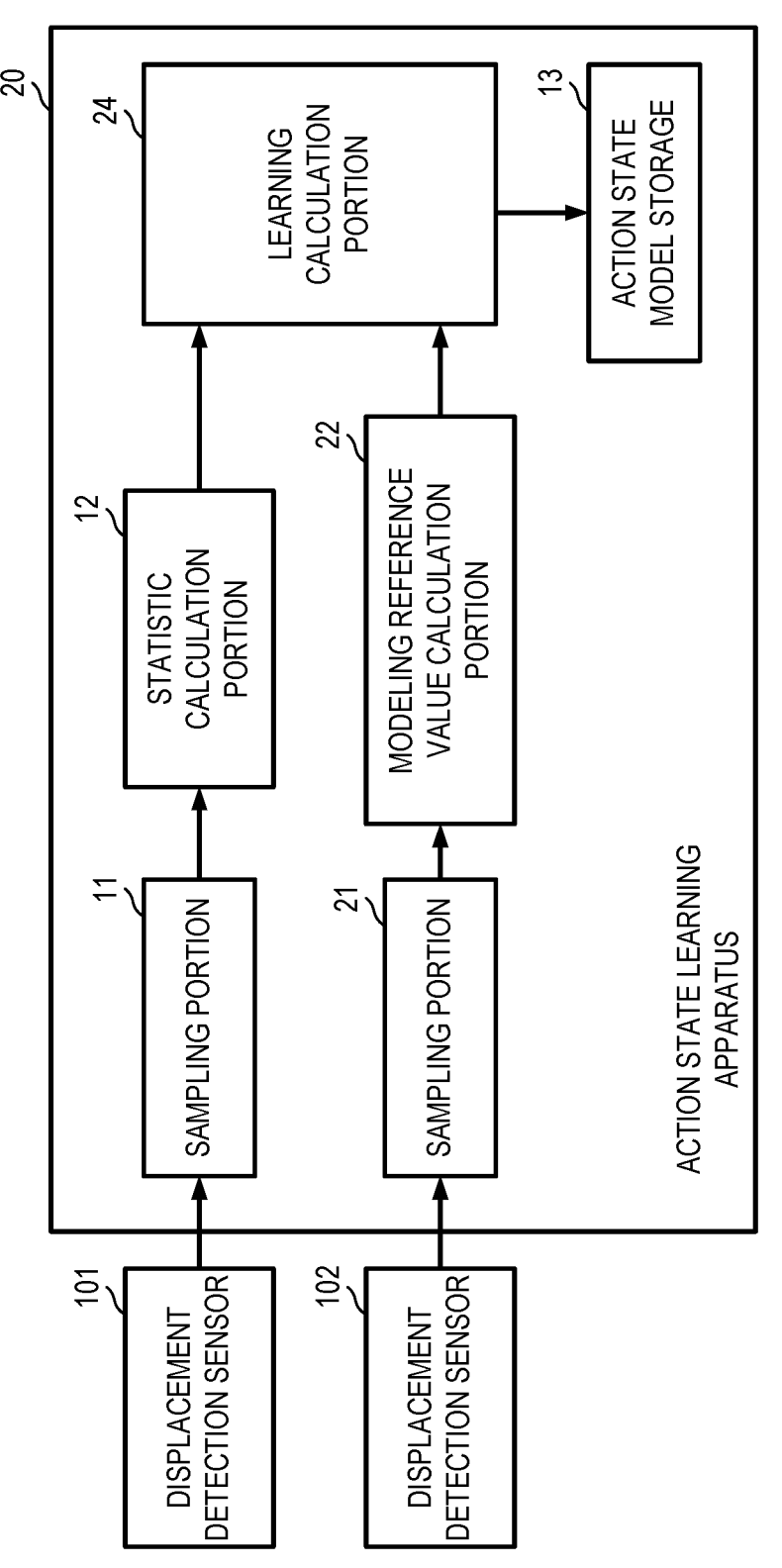
FIG. 4 is a functional block diagram of an action state learning apparatus according to the first exemplary embodiment.

The above action state model is generated, for example, as shown below. FIG. 4 is a functional block diagram of the action state learning apparatus according to the first exemplary embodiment of the present invention.

As shown in FIG. 4, the action state learning apparatus 20 includes a sampling portion 11, a statistic calculation portion 12, an action state model storage 13, a sampling portion 21, a modeling reference value calculation portion 22, and a learning calculation portion 24. The sampling portion 11, the statistic calculation portion 12, and the action state model storage 13 are as described above, and thus the description will be omitted.

In operation, the sampling portion 21 receives an input of a muscle activity measurement signal (e.g., a muscle potential signal, for example) from the muscle activity detection sensor 102. The sampling portion 21 generates muscle activity measurement data by sampling the muscle activity measurement signal by a predetermined sampling frequency (100 Hz, for example). The sampling portion 21 then outputs the muscle activity measurement data to the modeling reference value calculation portion 22.

It is noted that the muscle activity detection sensor 102 is a sensor configured for measuring muscle activity, for example, is a myoelectric sensor (e.g., an electromyograph). The muscle activity detection sensor 102 is disposed at a position of a muscle of which the loaded state is to be estimated. More specifically, the muscle activity detection sensor 102 is disposed at a position of a muscle that is a source of muscle activity that produces a tremor to be measured by the muscle activity detection sensor 102. The muscle activity detection sensor 102 detects muscle activity, and generates and outputs a muscle activity measurement signal. In an exemplary aspect, the muscle activity detection sensor 102 can be a single sensor disposed with respect to one type of muscles or can be two or more sensors disposed according to a muscle with respect to a plurality of types of muscles.

The modeling reference value calculation portion 22 calculates a modeling reference value from the muscle activity measurement data. For example, the modeling reference value calculation portion 22 calculates an absolute average value of the muscle activity measurement data within a predetermined period as the modeling reference value. The absolute average value refers to an average value of an absolute value of the measurement data.

It is noted that the modeling reference value is not limited to the absolute average value and may use a regressionable value such as, for example, an average value, a maximum value, a minimum value, a median value, a 1% value, a 5% value, a 25% value, a 75% value, a 95% value, a 99% value, a variance value, a skewness value, or a kurtosis value. Furthermore, the modeling reference value is able to represent a class of a load, such as large, medium, or small, that is able to be classified from the muscle activity measurement data.

The modeling reference value calculation portion 22 outputs the modeling reference value to the learning calculation portion 24.

The learning calculation portion 24 performs learning by using the statistic and the modeling reference value, and generates an action state model. More specifically, for example, the learning calculation portion 24 performs learning by setting the statistic as an explanatory variable and the modeling reference value as an objective variable and using a gradient boosting method that utilizes a decision tree algorithm. The learning calculation portion 24 repeats the learning, and, when obtaining a predetermined inference accuracy, generates an action state model by using such a result. It is noted that a method of learning is not limited to the gradient boosting method, and may also use a method such as boosting represented by a similar AdaBoost method. In addition, other methods of learning may use an SVM, a GMM, an HMM, a neural network, a learning Bayesian network, or the like. Furthermore, by use of a plurality of learning devices as the learning calculation portion 24, an ensemble method that weights a result of the plurality of learning devices and then performs majority voting may be used.

With the configuration and processing, the action state learning apparatus 20 is configured to properly set the action state model.

(Method of Generating Action State Model)

Figure 5:
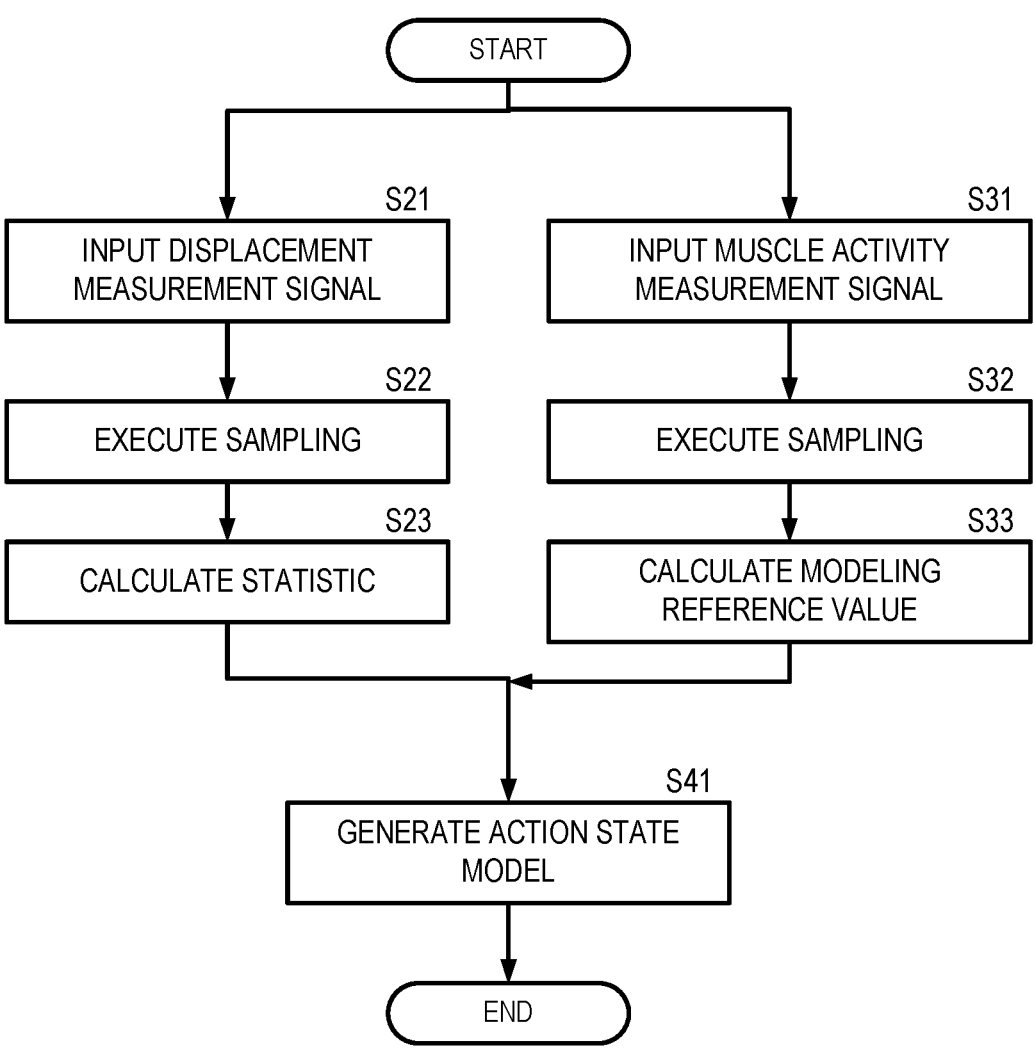
FIG. 5 is a flow chart showing a main process of an action state learning method according to the first exemplary embodiment.

FIG. 5 is a flow chart showing a main process of an action state learning method according to the first exemplary embodiment of the present invention. It is noted that, since the specific content of each processing is described by the above configurations, the following will be schematically described below.

The action state learning apparatus 20 inputs a displacement measurement signal (S21). The action state learning apparatus 20 executes sampling to the displacement measurement signal, and generates displacement measurement data (S22). The action state learning apparatus 20 calculates a statistic from the displacement measurement data (S23).

The action state learning apparatus 20 inputs a muscle activity measurement signal (S31). The action state learning apparatus 20 executes sampling to the muscle activity measurement signal, and generates muscle activity measurement data (S32). The action state learning apparatus 20 calculates a modeling reference value from the muscle activity measurement data (S33).

The action state learning apparatus 20 executes learning using the statistic and the modeling reference value, and generates an action state model (S41).

It is noted that the above processing may be programmed and stored in a storage medium or the like, and may be executed by an arithmetic processing apparatus such as a CPU, as described above.

In addition, as seen from the configurations of the action state estimation apparatus 10 and the action state learning apparatus 20 according to the present exemplary embodiment, by use of the configuration according to the present exemplary embodiment, during learning, a highly accurate action state model can be generated although it is necessary to use a relatively large-scale muscle potential measurement means such as an electromyograph, whereas, during actual use (when the action state estimation apparatus 10 is in use), it is unnecessary to use a relatively large-scale muscle potential measurement means such as an electromyograph. In other words, during actual use, with a simple configuration, a loaded state is able to be estimated (measured) with a little burden on a test subject.

Second Exemplary Embodiment

An action state estimation technology and an action state model generation technology according to a second exemplary embodiment will be described with reference to the drawings. The action state estimation technology according to the second exemplary embodiment is different in a method of calculating a statistic from the action state estimation technology shown in the first exemplary embodiment. FIG. 6A shows an example of time variation of signal strength, FIG. 6B shows signal strength distribution, and FIG. 6C shows strength block data.

The statistic calculation portion 12 calculates signal strength distribution from displacement measurement data within a predetermined period. The signal strength distribution refers to the displacement measurement data within a predetermined period that are arranged in order of increasing signal strength. For example, the statistic calculation portion 12, as shown in FIG. 6A, when obtaining the signal strength of time t1 to time t100 set by a predetermined sampling period (e.g., a sampling frequency), as shown in FIG. 6B, sets a rank R1 to a rank R100 in order of increasing signal strength and arranges ranks in order from the rank R1 to the rank R100.

The statistic calculation portion 12 generates strength block data from the signal strength distribution, and outputs the strength block data as a statistic. More specifically, the statistic calculation portion 12 sets a strength block (e.g., a signal strength block) for each predetermined number in order of increasing signal strength against the signal strength distribution. The statistic calculation portion 12 calculates an integrated value for each strength block, and generates the strength block data. For example, in the case of FIG. 6C, the statistic calculation portion 12 divides the measurement data into blocks of 10 pieces each. In one example, the statistic calculation portion 12 sets the signal strength from the rank R1 to the rank R10 as a strength block B1, and calculates an integrated value of the signal strength from the rank R1 to the rank R10. The statistic calculation portion 12 performs such processing from the strength block B1 to a strength block B10, and outputs a result as a statistic.

The estimation calculation portion 14 then estimates an action state by using the statistic based on the signal strength distribution. In such a case, the estimation calculation portion 14 estimates an action state by using the level of importance.

FIG. 7 is a table showing an example of a setting of the level of importance according to the second exemplary embodiment. As shown in FIG. 7, in the second exemplary embodiment, the level of importance is set for each muscle, to the strength block of the signal strength distribution.

For example, in the case of FIG. 7, with respect to the muscle M1, the level of importance to the estimation is set to an order of the strength block B10, the strength block B9, the strength block B6, the strength block B3, and the strength block B5 in order of the first place, the second place, the third place, the fourth place, and the fifth place. In addition, with respect to the muscle M2, the level of importance to the estimation is set to an order of the strength block B10, the strength block B8, the strength block B9, the strength block B7, and the strength block B1 in order of the first place, the second place, the third place, the fourth place, and the fifth place. Hereinafter, with respect to the muscle M3 and the muscle M4 as well, as shown in FIG. 7, the level of importance is set to the statistic (e.g., the strength block).

The estimation calculation portion 14, when setting a muscle to be estimated, estimates a loaded state of the muscle from a plurality of statistics (e.g., values of the strength block), by using the level of importance that is set according to the muscle.

With this configuration, the action state estimation apparatus according to the second exemplary embodiment, as with the action state estimation apparatus 10 according to the first exemplary embodiment, is configured to estimate a loaded state of the muscle without performing processing to convert the measurement data into a frequency component. As a result, the action state estimation apparatus significantly reduces a processing load while achieving a necessary estimation accuracy.

It is noted that, in the above description (see FIG. 6A, FIG. 6B, and FIG. 6C), the plurality of measurement data are arranged in order of strength, the plurality of strength blocks are set, and an integrated value is calculated for each of the plurality of strength blocks and used as a statistic. However, in such a case, the integrated value can be replaced with an average value.

Furthermore, in an aspect to be described below with reference to FIG. 8A, FIG. 8B, and FIG. 8C, a plurality of blocks (e.g., time blocks) are set to the plurality of measurement data in a time range, and an average value or an integrated value is calculated for each of the plurality of time blocks and used as a statistic.

When using an average value, the statistic calculation portion 12 divides the plurality of measurement data within time for statistic calculation into a time-series block (e.g., a time block), and calculates an average value for each time block. When using an integrated value, the statistic calculation portion 12 divides the plurality of measurement data within time for statistic calculation into a time-series block (e.g., a time block), and calculates an integrated value for each time block. The statistic calculation portion 12 then sets the average value or the integrated value as a value (e.g., a statistic) of the time block.

FIG. 8A shows an example of time variation of signal strength, FIG. 8B shows time block data (e.g., an average value), and FIG. 8C is a view showing time block data (e.g., an integrated value).

For example, when the measurement data as shown in FIG. 8A is obtained, time blocks B1t to B10t arranged over time are set with respect to the signal strength from the time t1 to the time t100. The time block B1t corresponds to time t1 to t10, and the time block B2t corresponds to the time t11 to the time t20. Similarly, the time blocks B3t to B9t are set, and the time block B10t corresponds to the time t91 to the time t100.

When using an average value, for the time block B1t, the statistic calculation portion 12 calculates an average value of the signal strength of the time t1 to the time t10, and sets the average value as a statistic of the time block B1t. Similarly, the statistic calculation portion 12 calculates an average value of the time blocks B2t to B9t, and sets the average value as each statistical value. Then, the statistic calculation portion 12, for the time block B10t, calculates an average value of the signal strength of the time t91 to the time t100, and sets the average value as a statistic of the time block B10t.

When using an integrated value, for the time block B1t, the statistic calculation portion 12 calculates an integrated value of the signal strength of the time t1 to the time t10, and sets the integrated value as a statistic of the time block B1t. Similarly, the statistic calculation portion 12 calculates an integrated value of the time blocks B2t to B9t, and sets the integrated value as each statistical value. Then, the statistic calculation portion 12, for the time block B10t, calculates an integrated value of the signal strength of the time t91 to the time t100, and sets the integrated value as a statistic of the time block B10t.

Third Exemplary Embodiment

An action state estimation technology and an action state model generation technology according to a third exemplary embodiment will be described with reference to the drawings.
(Configuration and Processing of Action State Estimation Apparatus)

Figure 9:
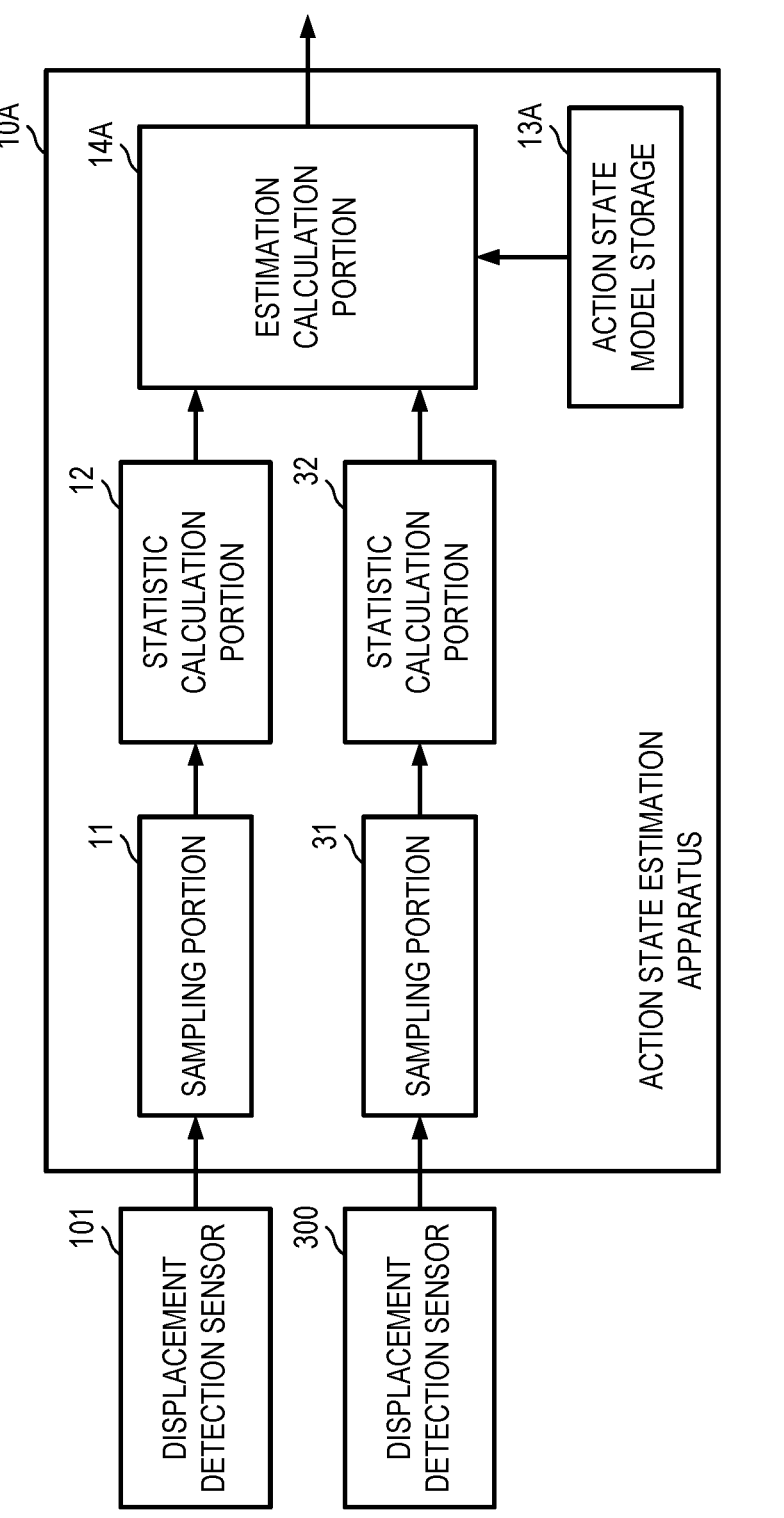
FIG. 9 is a functional block diagram of an action state estimation apparatus according to a third exemplary embodiment.

FIG. 9 is a functional block diagram of an action state estimation apparatus according to the third exemplary embodiment. As shown in FIG. 9, an action state estimation apparatus 10A is different from the action state estimation apparatus 10 according to the first exemplary embodiment in that a sampling portion 31, a statistic calculation portion 32, an action state model storage 13A, and an estimation calculation portion 14A are provided. Other configurations of the action state estimation apparatus 10A are the same as or similar to the configurations of the action state estimation apparatus 10, and a description of the same or similar configurations will be omitted.

As illustrated, the action state estimation apparatus 10A includes a sampling portion 11, a statistic calculation portion 12, an estimation calculation portion 14A, an action state model storage 13A, a sampling portion 31, and a statistic calculation portion 32. Each function portion configuring the action state estimation apparatus 10A can be implemented by an electronic circuit, an IC, a storage medium storing a program to execute a function of each function portion, and a calculation processing device (such as a CPU) that executes the program as similarly described above with respect to the first exemplary embodiment.

In operation, the statistic calculation portion 12 calculates the statistic shown in the first exemplary embodiment as a displacement statistic, and outputs the statistic to the estimation calculation portion 14A.

The sampling portion 31 receives an input of a motion measurement signal from a motion detection sensor 300. The sampling portion 31 generates motion measurement data by sampling the motion measurement signal by a predetermined sampling frequency (100 Hz, for example). In other words, the sampling portion 31 generates the motion measurement data without converting the motion measurement signal into a frequency component. The sampling portion 31 outputs the motion measurement data to the statistic calculation portion 32.

It is noted that the motion detection sensor 300 is used by using an acceleration sensor, an angular velocity sensor, or the like. The motion detection sensor 300 does not need to be disposed at a position of a muscle of which the loaded state is estimated, and may be disposed at a position at which a motion of a test subject to occur by the muscle to be estimated is able to be measured. In addition, the motion detection sensor 300 may be one sensor disposed at one location place or may be two or more sensors disposed at two or more locations. The motion detection sensor 300 is configured to detect the motion of a test subject, and generates and outputs a motion measurement signal.

The statistic calculation portion 32 calculates a motion statistic from the motion measurement data arranged in time series. In particular, the statistic calculation portion 32 calculates a motion statistic from a plurality of motion measurement data within a predetermined period (for 1 second, for example).

Types of motion statistics include, for example, an average value, a maximum value, a minimum value, a median value, a 1% value, a 5% value, a 25% value, a 75% value, a 95% value, a 99% value, a variance value, a skewness value, a kurtosis value, and an integrated value. It is to be noted that the types of motion statistics are not limited to these examples, and may be others as long as a value is obtained from time-series motion measurement data. The statistic calculation portion 32 calculates a plurality of types of motion statistics out of these values. It is to be noted that an x % value refers to a value that corresponds to the top x % of the maximum value 100% of the plurality of motion measurement data within a period.

The statistic calculation portion 32 outputs the plurality of types of motion statistics that have been calculated, to the estimation calculation portion 14A.

The action state model storage 13A stores an action state model that includes a relationship between various types of displacement statistics and various types of motion statistics, and a loaded state of a muscle to be estimated. The action state model is previously generated by an action state learning apparatus 20A to be described below, for example, and is stored (e.g., contained) in the action state model storage 13A in an exemplary aspect.

The estimation calculation portion 14A estimates the loaded state of a muscle to be estimated by using the action state model stored in the action state model storage 13A and setting a displacement statistic and a motion statistic as an input vector. In such a case, the estimation calculation portion 14A sets a level of importance of the displacement statistic and a level of importance of the motion statistic that are used for estimation, according to the muscle to be estimated. The levels of importance are set to the action state model, for example.

FIG. 10A and FIG. 10B are tables showing an example of a setting of the level of importance according to the third exemplary embodiment. FIG. 10A shows the level of importance of the displacement statistic, and FIG. 10B shows the level of importance of the motion statistic. In addition, in FIG. 10A and FIG. 10B, a muscle M1, a muscle M2, a muscle M3, and a muscle M4 show a type of muscles of which the loaded state is able to be estimated by measured displacement. For example, in a case in which the displacement detection sensor 101 is disposed at a place at which tendons of an ankle are gathered, more specifically, in front of the ankle and in back of the ankle, the muscle M1, the muscle M2, the muscle M3, and the muscle M4 are able to set a soleus muscle, a gastrocnemius muscle, a tibialis anterior muscle, a quadriceps femoris muscle, a hamstring muscle, or the like. Each of the displacement statistics Ar1 to Ar15 is set to any one of the above various types of displacement statistics, and each of the motion statistics Aa1 to Aa15 is set to any one of the above various types of motion statistics.

For example, in the case of FIG. 10A, with respect to the muscle M1, the level of importance to the estimation is set to an order of the displacement statistic Ar1, the displacement statistic Ar2, the displacement statistic Ar8, the displacement statistic Ar12, and the displacement statistic Ar7 in order of the first place, the second place, the third place, the fourth place, and the fifth place. In addition, with respect to the muscle M2, the level of importance to the estimation is set to the order of the displacement statistic Ar3, the displacement statistic Ar5, the displacement statistic Ar2, the displacement statistic Ar14, and the displacement statistic Ar15 in order of the first place, the second place, the third place, the fourth place, and the fifth place. Hereinafter, with respect to the muscle M3 and the muscle M4 as well, as shown in FIG. 10A, the level of importance is set to the displacement statistic.

Furthermore, in the case of FIG. 10B, for example, with respect to the muscle M1, the level of importance to the estimation is set to an order of the motion statistic Aa1, the motion statistic Aa2, the motion statistic Aa8, the motion statistic Aa12, and the motion statistic Aa7 in order of the first place, the second place, the third place, the fourth place, and the fifth place. In addition, with respect to the muscle M2, the level of importance to the estimation is set to the order of the motion statistic Aa3, the motion statistic Aa5, the motion statistic Aa2, the motion statistic Aa14, and the motion statistic Aa15 in order of the first place, the second place, the third place, the fourth place, and the fifth place. Hereinafter, with respect to the muscle M3 and the muscle M4 as well, as shown in FIG. 10B, the level of importance is set to the motion statistic.

It is noted that the level of importance of the displacement statistic and the level of importance of the motion statistic with respect to one type of muscles may be set by a common level of importance or may be set individually according to various exemplary aspects. For example, in a case in which an index (e.g., a number) of the displacement statistic and an index (e.g., a number) of the motion statistic that are shown in FIG. 10A and FIG. 10B show the same type of a statistic, the level of importance of the displacement statistic and the level of importance of the motion statistic shown in FIG. 10A and FIG. 10B are able to be set by the common level of importance.

On the other hand, when the index (e.g., the number) of the displacement statistic shown in FIG. 10A is set according to the type of the displacement statistic and the index (e.g., the number) of the motion statistic shown in FIG. 10B is set according to the type of the motion statistic, the setting of the level of importance of the displacement statistic and the level of importance of the motion statistic are set individually.

According to an exemplary aspect, the level of importance of the displacement statistic and the level of importance of the motion statistic are set by the common level of importance, which makes it possible to simplify the setting of the level of importance and also simplify the estimation processing of an action state. On the other hand, the level of importance of the displacement statistic and the level of importance of the motion statistic are set individually, which makes it possible to set more various conditions to estimate an action state and estimate an action state with a further higher accuracy.

The estimation calculation portion 14A, when setting the muscle to be estimated, estimates a loaded state (e.g., a muscle potential value) of the muscle from a plurality of displacement statistics and a plurality of motion statistics, by using the level of importance that is set according to the muscle. It is noted that the loaded state of the muscle is not limited to the muscle potential value and may be any other data that can be expressed as a value.

More specifically, for example, the estimation calculation portion 14A calculates an estimation result of a loaded state from a pair of the displacement statistic of the motion statistic of the same rank in the level of importance and the action state model. The estimation calculation portion 14A calculates the estimation result of a loaded state for each pair of the same rank in the level of importance. Then, the estimation calculation portion 14A weights each estimation result according to the level of importance, and calculates the estimation result of a final loaded state by performing addition averaging or the like, for example.

It is noted that the estimation calculation portion 14A is configured to individually calculate an estimation result of a loaded state from the displacement statistic and the action state model, and an estimation result of a loaded state from the motion statistic and the action state model, and is also configured to calculate an estimation result of a final loaded state from the estimation results. The number of displacement statistics and motion statistics that are used by the estimation calculation portion 14A for estimation is not limited to this example and is able to be set properly. For example, estimation calculation may be performed from the statistics ranked from the first place to the tenth place in the level of importance.

The estimation calculation portion 14A, when the number of types of the muscle to be estimated is one, estimates a loaded state by using the displacement statistic and the motion statistic and the level of importance according to the muscle. On the other hand, the estimation calculation portion 14A, when the number of types of the muscle to be estimated is two or more, for each muscle, sets the displacement statistic and the motion statistic and the level of importance in each case and estimates a loaded state with respect to each muscle.

With this configuration, the action state estimation apparatus 10A is configured to estimate a loaded state of a muscle by using a detection result of not only displacement including a tremor, but also a motion such as acceleration, angular velocity, or the like. The detection result of the motion such as sampled acceleration, angular velocity, or the like is strongly influenced by the motion of a test subject, and is highly correlated to muscle activity of the test subject. Then, since the action state estimation apparatus 10A, since estimating an action state from microscopic tremor measurement data and macroscopic motion measurement data, estimates the loaded state of a muscle with a high accuracy.

Furthermore, in this configuration, the displacement measurement data are also sampled measurement data. Therefore, the action state estimation apparatus 10A significantly reduces lack of information on a tremor associated with frequency conversion, and is configured to estimate the loaded state of a muscle with higher accuracy.

Furthermore, in such a configuration, the action state estimation apparatus 10A, for each muscle to be estimated, individually sets the type of displacement statistic and the motion statistic that are used for estimation, and the level of importance. As a result, the action state estimation apparatus 10A is configured to estimate the loaded state of a muscle with a much higher accuracy.

In addition, with such a configuration, the action state estimation apparatus 10A, even when the position of the displacement detection sensor 101 and a position of the motion detection sensor 300 are not at a position of a muscle to be estimated, is configured to estimate the loaded state of the muscle. As a result, the action state estimation apparatus

10A is also configured to estimate the loaded state with respect to a muscle that is not appeared on a body surface or a muscle (e.g., a muscle away from a position in which the displacement detection sensor 101 or the motion detection sensor 300 is disposed) for which the muscle potential is not able to be directly measured. The displacement detection sensor 101 and the motion detection sensor 300 are disposed on an ankle, so that the action state estimation apparatus 10A is able to estimate the loaded state of a quadriceps femoris muscle, a hamstring muscle (e.g., a biceps femoris muscle, a semimembranosus muscle, a semitendinosus muscle, an adductor magnus muscle), a tibialis anterior muscle, a gastrocnemius muscle, a soleus muscle, and a gluteus maximus muscle. In addition, the action state estimation apparatus 10A is configured to estimate a linked state of a plurality of muscles.

Moreover, an effect due to an error in the position in which the displacement detection sensor 101 is disposed is significantly reduced. Therefore, the disposition of the displacement detection sensor 101 and the motion detection sensor 300 is facilitated, and an operation for estimation of a loaded state is facilitated.

In addition, with such a configuration, the loaded state of a plurality of muscles can be estimated, using the displacement measurement signal of the displacement detection sensor 101 and the motion measurement signal of the motion detection sensor 300 in common, so that an action state estimation system including a sensor and the action state estimation apparatus can be reduced in size.

Moreover, in such a configuration, the displacement statistic and the motion statistic that are used and the level of importance are individually set for each muscle to be estimated. Therefore, the action state estimation apparatus 10A is configured to estimate the loaded state of a plurality of muscles with a high accuracy by using a measurement signal of the displacement detection sensor 101 and a measurement signal of the motion detection sensor 300 in common.

In addition, with such a configuration, a loaded state can be estimated not as a class but as a value. In this manner, a loaded state is estimated with a value, so that the action state estimation apparatus 10A is configured to present and manage a more accurate loaded state, and is configured to provide more appropriate notification or the like, to a test subject.

(Action State Estimation Method)

Figure 11:
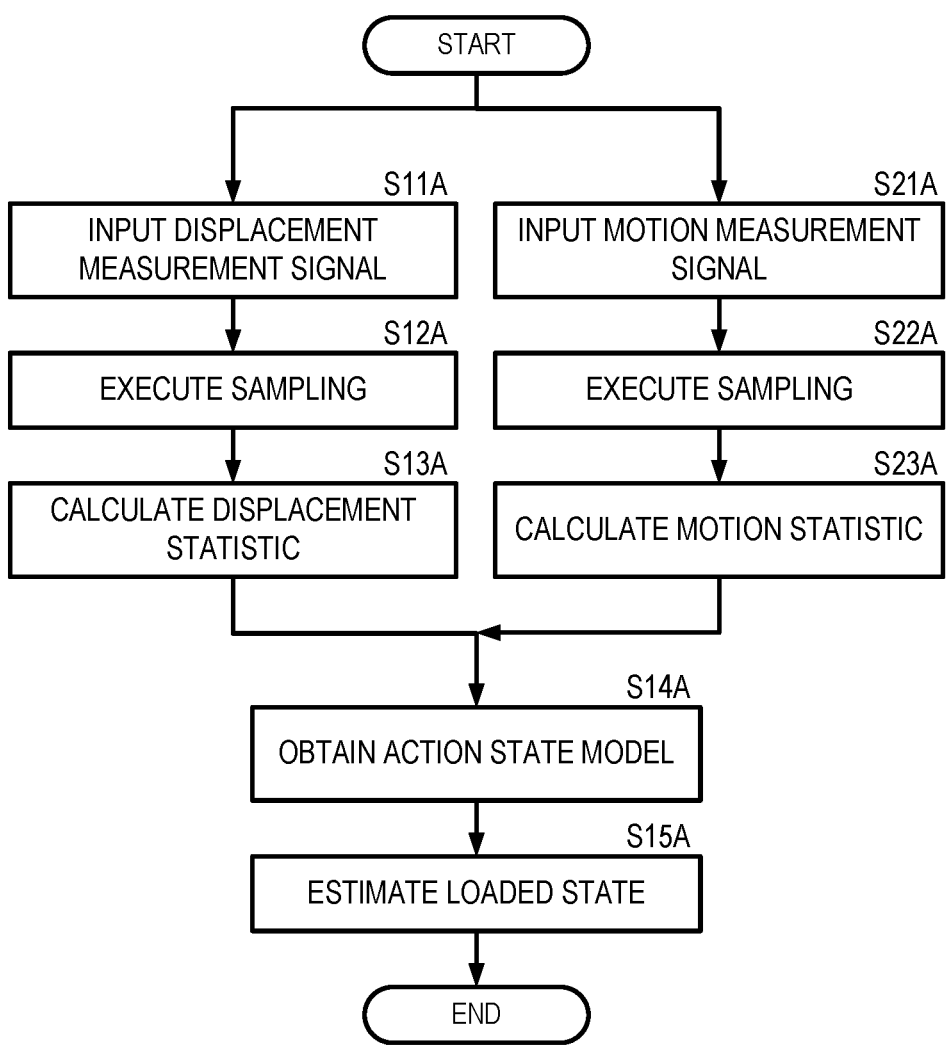
FIG. 11 is a flow chart showing a main process of an action state estimation method according to the third exemplary embodiment.

FIG. 11 is a flow chart showing a main process of an action state estimation method according to the third exemplary embodiment. It is noted that, since the specific content of each processing is described by the above configurations, the following will be schematically described below.

The action state estimation apparatus 10A inputs a displacement measurement signal (S11A). The action state estimation apparatus 10A executes sampling to the displacement measurement signal, and generates displacement measurement data (S12A). The action state estimation apparatus 10A calculates a displacement statistic from the displacement measurement data (S13A).

The action state estimation apparatus 10A inputs a motion measurement signal (S21A). The action state estimation apparatus 10A executes sampling to the motion measurement signal, and generates motion measurement data (S22A). The action state estimation apparatus 10A calculates a motion statistic from the motion measurement data (S23A).

The action state estimation apparatus 10A obtains an action state model (S14A). The action state estimation apparatus 10A estimates a loaded state by using the action state model and setting the displacement statistic and the motion statistic as an input vector (S15A).

It is noted that the above processing may be programmed and stored in a storage medium or the like, and may be executed by an arithmetic processing apparatus such as a CPU, as described above, for example.

(Configuration and Processing of Action State Learning Apparatus)

Figure 12:
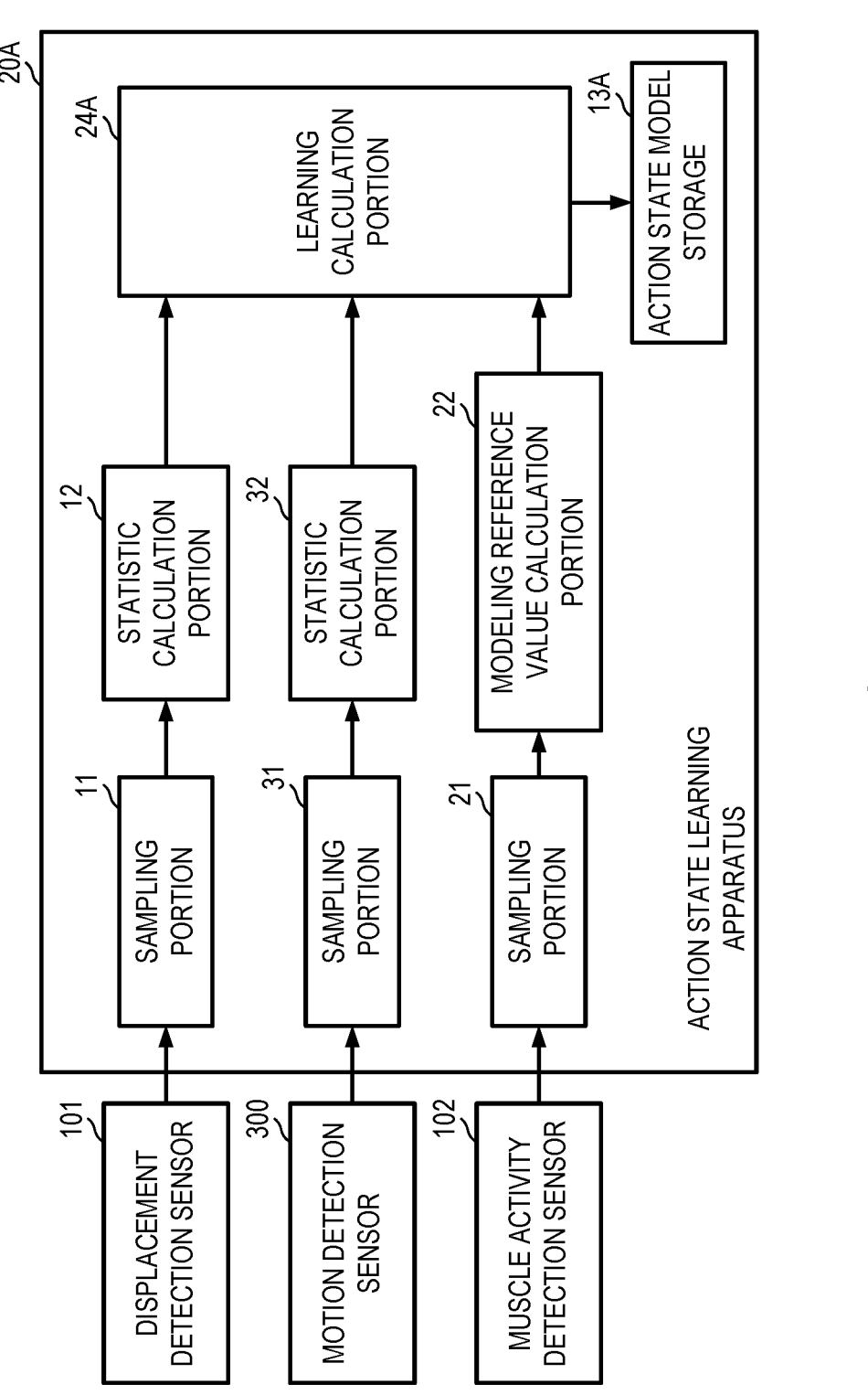
FIG. 12 is a functional block diagram of an action state learning apparatus according to the third exemplary embodiment.

The above action state model is generated, for example, as shown below. FIG. 12 is a functional block diagram of an action state learning apparatus according to the third exemplary embodiment.

As shown in FIG. 12, the action state learning apparatus 20A includes a sampling portion 11, a statistic calculation portion 12, an action state model storage 13A, a sampling portion 21, a modeling reference value calculation portion 22, a learning calculation portion 24A, a sampling portion 31, and a statistic calculation portion 32. The sampling portion 11, the statistic calculation portion 12, the action state model storage 13A, the sampling portion 31, and the statistic calculation portion 32 are as described above, and thus the description will be omitted.

In operation, the sampling portion 21 receives an input of a muscle activity measurement signal (e.g., a muscle potential signal) from the muscle activity detection sensor 102. The sampling portion 21 generates muscle activity measurement data by sampling the muscle activity measurement signal by a predetermined sampling frequency (100 Hz, for example). The sampling portion 21 outputs the muscle activity measurement data to the modeling reference value calculation portion 22.

It is noted that the muscle activity detection sensor 102 is a sensor configured to measure muscle activity, for example, is a myoelectric sensor (e.g., an electromyograph). The muscle activity detection sensor 102 is disposed at a position of a muscle of which the loaded state is to be estimated. More specifically, the muscle activity detection sensor 102 is disposed at a position of a muscle that is a source of muscle activity that produces a tremor to be measured by the muscle activity detection sensor 102. The muscle activity detection sensor 102 detects muscle activity, and generates and outputs a muscle activity measurement signal. The muscle activity detection sensor 102 can be a single sensor disposed with respect to one type of muscles or can be two or more sensors disposed according to a muscle with respect to a plurality of types of muscles.

The modeling reference value calculation portion 22 calculates a modeling reference value from the muscle activity measurement data. For example, the modeling reference value calculation portion 22 calculates an absolute average value of the muscle activity measurement data within a predetermined period as the modeling reference value. The absolute average value refers to an average value of an absolute value of the measurement data.

It is noted that the modeling reference value is not limited to the absolute average value and may use a regressionable value such as, for example, an average value, a maximum value, a minimum value, a median value, a 1% value, a 5% value, a 25% value, a 75% value, a 95% value, a 99% value, a variance value, a skewness value, or a kurtosis value. Furthermore, the modeling reference value is able to represent a class of a load, such as large, medium, or small, that is able to be classified from the muscle activity measurement data.

The modeling reference value calculation portion 22 outputs the modeling reference value to the learning calculation portion 24A.

The learning calculation portion 24A is configured to perform learning by using the displacement statistic and the motion statistic, and the modeling reference value, and generates an action state model. More specifically, for example, the learning calculation portion 24A performs learning by setting the displacement statistic and the motion statistic as an explanatory variable and the modeling reference value as an objective variable and using a gradient boosting method that utilizes a decision tree algorithm. The learning calculation portion 24A repeats the learning, and, when obtaining a predetermined inference accuracy, generates an action state model by using such a result.

It is noted that a method of learning is not limited to the gradient boosting method, and may also use a method such as boosting represented by a similar AdaBoost method according to alternative exemplary aspects. In addition, other methods of learning may use an SVM, a GMM, an HMM, a neural network, a learning Bayesian network, or the like.

Furthermore, by use of a plurality of learning devices as the learning calculation portion 24A, an ensemble method that weights a result of the plurality of learning devices and then performs majority voting may be used.

With the configuration and processing, the action state learning apparatus 20A is able to properly set the action state model.

(Action State Learning Method)

Figure 13:
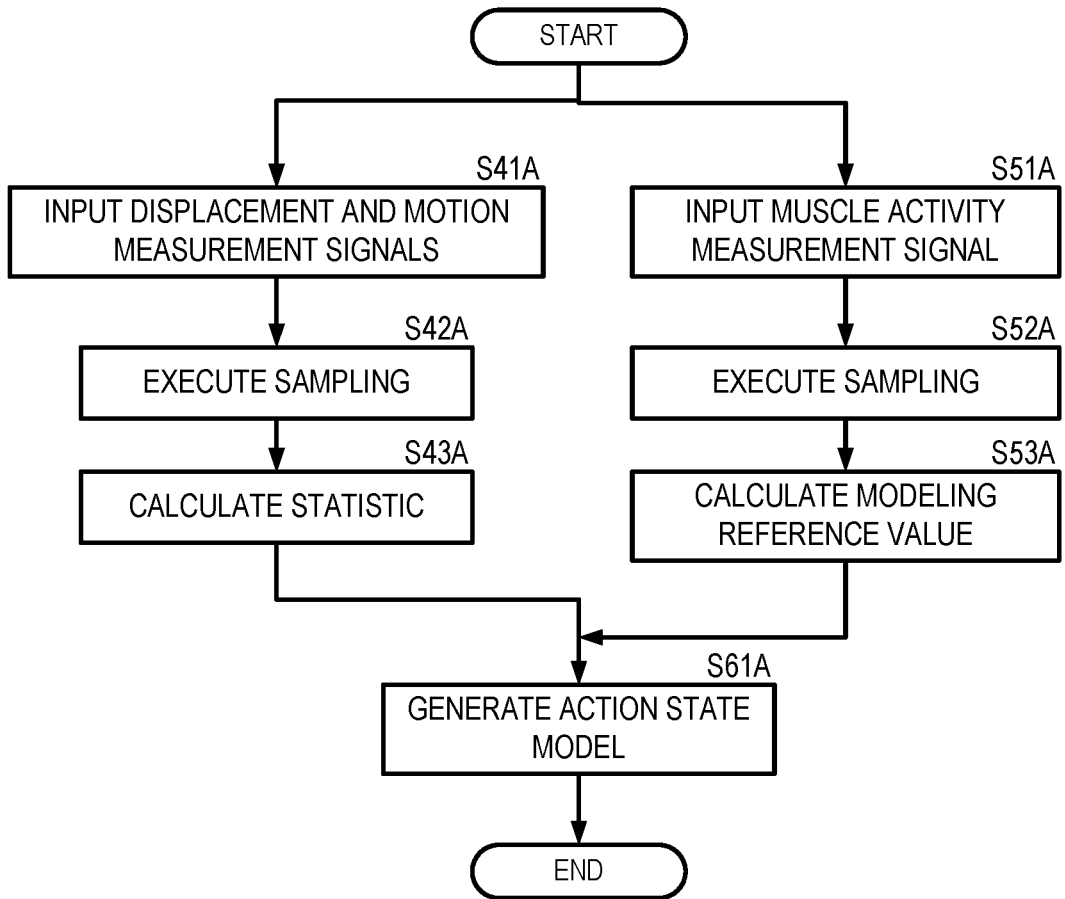
FIG. 13 is a flow chart showing a main process of an action state learning method according to the third exemplary embodiment.

FIG. 13 is a flow chart showing a main process of an action state learning method according to the third exemplary embodiment.

In operation, the action state learning apparatus 20A inputs a displacement measurement signal and a motion measurement signal (S41A). The action state learning apparatus 20A executes sampling to the displacement measurement signal, generates displacement measurement data, executes sampling to a motion measurement signal, and generates motion measurement data (S42A). The action state learning apparatus 20A calculates a displacement statistic from the displacement measurement data, and calculates a motion statistic from the motion measurement data (S43A).

The action state learning apparatus 20A inputs a muscle activity measurement signal (S51A). The action state learning apparatus 20A executes sampling to the muscle activity measurement signal, and generates muscle activity measurement data (S52A). The action state learning apparatus 20A calculates a modeling reference value from the muscle activity measurement data (S53A).

The action state learning apparatus 20A executes learning using the displacement statistic and the motion statistic, and the modeling reference value, and generates an action state model (S61A).

It is noted that the above processing may be programmed and stored in a storage medium or the like, and may be executed by an arithmetic processing apparatus such as a CPU, as described above, for example.

Fourth Exemplary Embodiment

An action state estimation technology and an action state model generation technology according to a fourth exemplary embodiment will be described. The action state estimation technology according to the fourth exemplary embodiment is different from the action state estimation technology shown in the third exemplary embodiment in that strength block data of the displacement statistic and the motion statistic is used. A method of generating the strength block data of the motion statistic is the same as or similar to the method of generating the strength block data of the displacement statistic according to the third exemplary embodiment, and thus the description using a specific example will be omitted.

The statistic calculation portion 12 generates strength block data (e.g., displacement strength block data) of displacement measurement data from signal strength distribution of the displacement measurement data, and outputs the strength block data as a displacement statistic. More specifically, the statistic calculation portion 12 sets a strength block (e.g., a signal strength block) for each predetermined number in order of increasing signal strength against the signal strength distribution. The statistic calculation portion 12 calculates an integrated value for each strength block, and generates the displacement strength block data.

It is noted that the statistic calculation portion 32 has the same or similar configuration as the statistic calculation portion 12, and performs the same processing as the statistic calculation portion 12, to the motion measurement data. As a result, the statistic calculation portion 32 calculates and outputs a motion statistic including the strength block data (e.g., motion strength block data) of the motion measurement data.

The estimation calculation portion 14A estimates an action state by using the displacement statistic and the motion statistic based on the signal strength distribution. In such a case, the estimation calculation portion 14A estimates an action state by using the level of importance.

FIG. 14A and FIG. 14B are tables showing an example of a setting of the level of importance according to the fourth exemplary embodiment. FIG. 14A shows the level of importance of the displacement statistic, and FIG. 14B shows the level of importance of the motion statistic. As shown in FIG. 14A and FIG. 14B, in the fourth exemplary embodiment, the level of importance is set for each muscle, to the strength block of the signal strength distribution.

The setting of the level of importance shown in FIG. 14A is the same as or similar to the setting of the level of importance shown in FIG. 10A except that the displacement statistic is a value of a strength block. The setting of the level of importance shown in FIG. 14B is the same as or similar to the setting of the level of importance shown in FIG. 10B except that the motion statistic is a value of a strength block. Therefore, the detailed description will be omitted.

The estimation calculation portion 14A, when setting a muscle to be estimated, estimates a loaded state of the muscle from a plurality of displacement statistics (e.g., values of the strength block) and a plurality of motion statistics (e.g., values of the strength block), by using the level of importance that is set according to the muscle.

With this configuration, the action state estimation apparatus according to the fourth exemplary embodiment, as with the action state estimation apparatus 10A according to the third exemplary embodiment, is configured to estimate the loaded state of the muscle with a high accuracy.

Fifth Exemplary Embodiment

An action state estimation technology and an action state model generation technology according to a fifth exemplary embodiment will be described with reference to the drawings. It is noted that the action state estimation technology according to the fifth exemplary embodiment is different from the action state estimation technology shown in the first exemplary embodiment in that a displacement measurement signal and a muscle activity measurement signal during learning are synchronized. Other methods of the action state estimation technology according to the fifth exemplary embodiment are the same as or similar to the methods of the action state estimation technology according to the first exemplary embodiment, and the description of the same or similar portions will be omitted.

Figure 15:
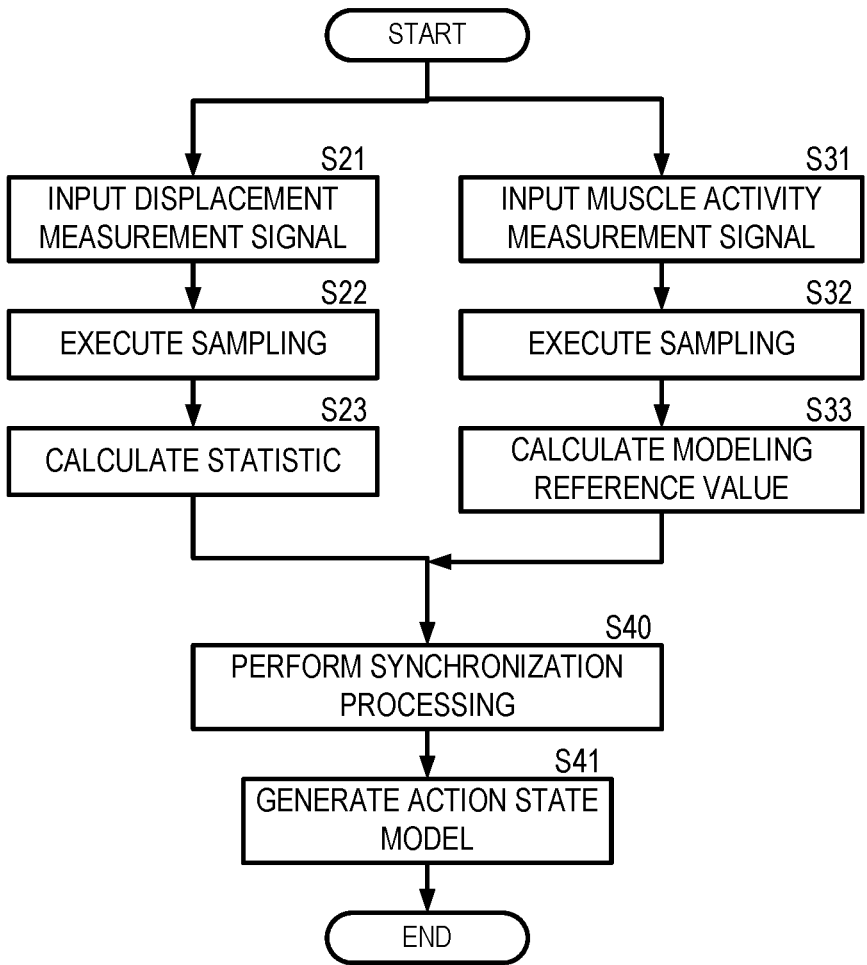
FIG. 15 is a flow chart showing a main process of an action state learning method according to a fifth exemplary embodiment.

FIG. 15 is a flow chart showing a main process of an action state learning method according to the fifth exemplary embodiment. As shown in FIG. 15, the action state learning method according to the fifth exemplary embodiment is different from the action state learning method according to the first exemplary embodiment in that synchronization processing is added. Other processing of the action state learning method according to the fifth exemplary embodiment is the same as or similar to the processing of the action state learning method according to the first exemplary embodiment, and the description of the same or similar processing will be omitted.

Figure 16:
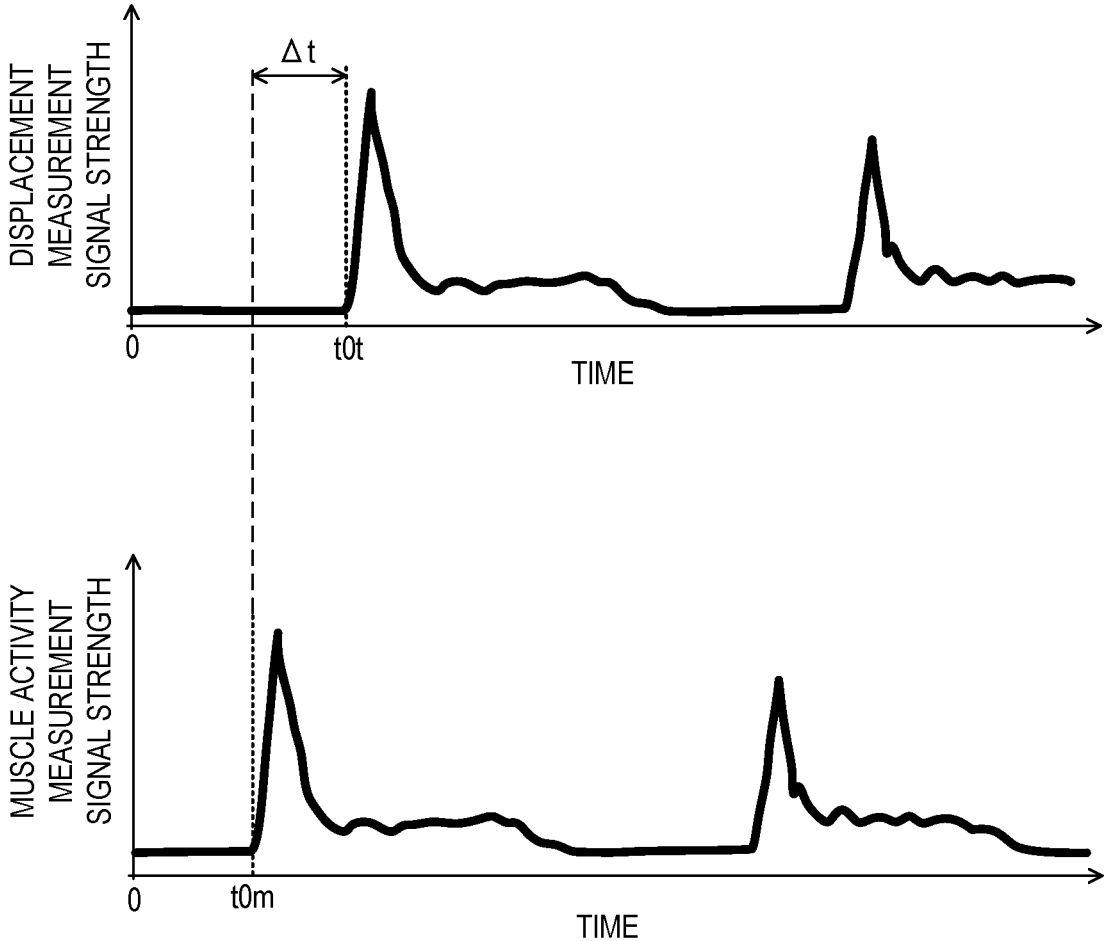
FIG. 16 shows a concept of synchronization.

The action state learning apparatus 20 calculates a statistic and a modeling reference value, and then synchronizes the statistic with the modeling reference value (S40). FIG. 16 shows a concept of synchronization. As shown in FIG. 16, according to a difference in reaction between the displacement detection sensor 101 and the muscle activity detection sensor 102, a time difference Δt occurs between reference time tot of a displacement measurement signal and reference time t0m of a muscle activity measurement signal.

Therefore, the learning calculation portion 24 detects the reference time t0t of a displacement measurement signal and the reference time t0m of a muscle activity measurement signal, and detects a time difference Δt by calculating the difference between the reference time t0t and the reference time t0m. The learning calculation portion 24 synchronizes the statistic with the modeling reference value by using the time difference Δt.

The learning calculation portion 24 performs learning by using the statistic and the modeling reference value that have been synchronized, and generates an action state model (S41).

By performing such processing, the action state estimation apparatus 10 is configured to estimate the loaded state of a muscle with higher accuracy.

It is also noted that, when the learning is performed by use of a displacement measurement signal and a motion measurement signal, and a muscle activity measurement signal, the displacement measurement signal and the motion measurement signal may be synchronized with the muscle activity measurement signal to perform the learning.

In general, it is noted that the configuration and processing of each of the above exemplary embodiments are able to be combined. Then, the use of such a combination enables the action state estimation apparatus and the action state estimation method to achieve a higher estimation accuracy. For example, two statistics of the statistic obtained by sampling and the statistic obtained by calculating signal strength distribution are used in combination (i.e., both statistics can be used).

In addition, the above description shows an aspect in which a myoelectric sensor (e.g., an electromyograph) is used as the muscle activity detection sensor 102. However, the muscle activity detection sensor 102 may be another sensor capable of measuring muscle activity such as MRI.

Moreover, the above description shows an aspect in which an inertia sensor such as an acceleration sensor or an angular velocity sensor is used as the motion detection sensor 300. However, the motion detection sensor 300 may also use a motion sensor, an imaging sensor, or the like, for example.

In addition, the above description shows an aspect in which the displacement measurement signal is sampled. However, when the motion measurement signal is sampled, it is also possible to frequency-sample the displacement measurement signal. However, as described above, by sampling the displacement measurement signal, the action state estimation apparatus is configured to estimate the loaded state of a muscle with higher accuracy.

In view of the foregoing, the displacement detection sensor 101 is preferably a piezoelectric sensor. In other words, while another sensor such as an acceleration sensor improves accuracy by extracting a frequency component, the use of the piezoelectric sensor enables accurate estimation even without such an extraction of a frequency component.

Moreover, the above configuration and processing show an aspect in which the loaded state of a muscle is estimated as an action state. However, other action states of a test subject who has relevance to the loaded state of the muscle are able to be estimated.

In addition, the above configuration and processing show an aspect in which an action state is estimated by use of the displacement statistic and the motion statistic that are obtained by sampling and by adding no change or by use of the displacement statistic and the motion statistic that are obtained by calculating signal strength distribution. However, the action state estimation apparatus and the action state estimation method are also able to use a difference value (e.g., a change amount) or a rate of change of each statistic. Specifically, the action state estimation apparatus and the action state estimation method calculate a difference value (e.g., a change amount) or a rate of change of adjacent statistics in a plurality of statistics, and use a calculated value. Accordingly, the action state estimation apparatus and the action state estimation method are also able to estimate variation in the action state.

In addition, in estimation of a loaded state using the above action state model, the following items related to biological information may be added as an input vector. For example, at least one of the following items: BMI, height, weight, body fat percentage, muscle mass, grip strength (left, right, the first time, the second time), lower thigh minimum circumference, age (20s, 30s, 40s, 50s, 60s), and gender (female, male) of a person to be measured, may be added. As a result, the loaded state of a muscle can be estimated with a higher accuracy.

REFERENCE SIGNS LIST

10, 10A: action state estimation apparatus
11: sampling portion
12: statistic calculation portion
13, 13A: action state model storage
14, 14A: estimation calculation portion
20, 20A: action state learning apparatus
21: sampling portion
22: modeling reference value calculation portion
24, 24A: learning calculation portion
31: sampling portion
32: statistic calculation portion
101: displacement detection sensor
102: muscle activity detection sensor
300: motion detection sensor

What is claimed:

1. An action state estimation apparatus comprising:
a first sampling portion configured to sample a displacement measurement signal of a test subject within a predetermined time and to generate displacement measurement data based on the sampled displacement measurement signal;
a first statistic calculation portion configured to calculate a first statistic of the displacement measurement data;
an action state model storage that stores an action state model that is modeled by associating the calculated first statistic with a loaded state of a muscle of the test subject; and
an estimation calculation portion configured to estimate the loaded state of the muscle by setting the first statistic as an input vector and using the action state model,
wherein the action state model is learned using the calculated first statistic of the displacement measurement data and a modeling reference value of the action state model, and
wherein the modeling reference value is calculated from a muscle activity measurement data that is generated by sampling a muscle activity measurement signal within a predetermined time.

2. The action state estimation apparatus according to claim 1, wherein the statistic calculation portion is configured to calculate the first statistic from a signal strength distribution obtained by arranging the displacement measurement data in order of increasing signal strength.

3. The action state estimation apparatus according to claim 2, wherein the statistic calculation portion is configured to divide the signal strength distribution into a plurality of signal strength blocks, and to use a statistic calculated for each signal strength block as the first statistic.

4. The action state estimation apparatus according to claim 1, wherein the statistic calculation portion is configured to divide the displacement measurement data into blocks for each predetermined time arranged in time series, and to use a statistic calculated for each block as the first statistic.

5. The action state estimation apparatus according to claim 1, wherein the action state model sets an importance level of the statistic for each muscle of the test subject of which the loaded state is to be estimated.

6. The action state estimation apparatus according to claim 1, further comprising:
a second sampling portion configured to sample a motion measurement signal of the test subject within a predetermined time and to generate motion measurement data based on the sampled motion measurement signal; and
a second statistic calculation portion configured to calculate a second statistic with respect to the motion measurement data,
wherein the action state model storage stores the action state model modeled by associating the first statistic, the second statistic, and the loaded state of the muscle of the test subject; and
wherein the estimation calculation portion is configured to estimate the loaded state by setting the first statistic and the second statistic as the input vector and using the action state model.

7. The action state estimation apparatus according to claim 6, wherein the second statistic calculation portion is configured to divide the motion measurement data into a plurality of blocks, and to use a statistic calculated for each block as the second statistic.

8. The action state estimation apparatus according to claim 6, wherein the action state model sets an importance level of the first statistic and an importance level of the second statistic, for each muscle of the test subject of which the loaded state is to be estimated.

9. The action state estimation apparatus according to claim 8, wherein the importance level of the first statistic and the importance level of the second statistic are set by a common importance level.

10. The action state estimation apparatus according to claim 8, wherein the importance level of the first statistic and the importance level of the second statistic are set individually.

11. The action state estimation apparatus according to claim 6, wherein the motion measurement signal is a measurement signal of at least one of acceleration and angular velocity.

12. The action state estimation apparatus according to claim 1, wherein the displacement measurement signal is a signal obtained from a displacement detection sensor that is configured to convert a displacement on a skin of a test subject due to an effect of a physiological tremor into a voltage.

13. The action state estimation apparatus according to claim 1, wherein the input vector further includes biological information.

14. An action state estimation method comprising:

sampling a displacement measurement signal of a test subject within a predetermined time and generating displacement measurement data based on the sampled displacement measurement signal;

calculating a first statistic of the displacement measurement data; and estimating a loaded state of a muscle of the test subject by using an action state model modeled by associating the calculated first statistic with the loaded state of the muscle and setting the first statistic as an input vector;

calculating a modeling reference value of the action state model from a muscle activity measurement data that is generated by sampling a muscle activity measurement signal within a predetermined time; and learning the action state model using the calculated first statistic of the displacement measurement data and the modeling reference value of the action state model.

15. The action state estimation method according to claim 14, further comprising:

sampling a motion measurement signal of the test subject within a predetermined time and generating motion measurement data based on the sampled motion measurement signal; and calculating a second statistic with respect to the motion measurement data by estimating the loaded state by using the action state model modeled by associating the first statistic, the second statistic, and the loaded state of the muscle of the test subject and setting the first statistic and the second statistic as the input vector.

16. An action state learning apparatus comprising:

a first sampling portion configured to sample a displacement measurement signal of a test subject within a predetermined time and to generate displacement measurement data based on the sampled displacement measurement signal;

a first statistic calculation portion configured to calculate a first statistic of the displacement measurement data;

a third sampling portion configured to sample a muscle activity measurement signal within a predetermined time and to generate muscle activity measurement data based on the sampled muscle activity measurement signal;

a modeling reference value calculation portion configured to calculate a modeling reference value of an action state model from the muscle activity measurement data; and a learning calculation portion configured to execute a learning using the first statistic and the modeling reference value and to generate the action state model based on the executed learning.

17. The action state learning apparatus according to claim 16, wherein the learning calculation portion is configured to generate the action state model by synchronizing the first statistic with the modeling reference value.

18. The action state learning apparatus according to claim 16, further comprising:

a second sampling portion configured to sample a motion measurement signal of the test subject within a predetermined time and to generate motion measurement data based on the sampled motion measurement signal; and a second statistic calculation portion configured to calculate a second statistic with respect to the motion measurement data, wherein the learning calculation portion is configured to generate the action state model by using the first statistic, the second statistic, and the modeling reference value.

19. The action state learning apparatus according to claim 18, wherein the learning calculation portion is configured to generate the action state model by synchronizing the first statistic, the second statistic, and the modeling reference value.

20. An action state learning method comprising:

sampling a displacement measurement signal of a test subject within a predetermined time and generating displacement measurement data based on the sampled displacement measurement signal;

calculating a first statistic of the displacement measurement data;

sampling a muscle activity measurement signal of the test subject within a predetermined time and generating muscle activity measurement data based on the sampled muscle activity measurement signal;

calculating a modeling reference value of an action state model from the generated muscle activity measurement data; and executing a learning using the first statistic and the modeling reference value and generating the action state model based on the executed learning.

21. The action state learning method according to claim 20, further comprising:

sampling a motion measurement signal of the test subject within a predetermined time and generating motion measurement data based on the sampled motion measurement signal;

calculating a second statistic with respect to the motion measurement data; and generating the action state model by using the first statistic, the second statistic, and the modeling reference value.

* * * * *